(12) United States Patent
Luo et al.

(10) Patent No.: US 11,407,987 B2
(45) Date of Patent: Aug. 9, 2022

(54) MANNANASE PMAN5A MUTANT HAVING IMPROVED HEAT RESISTANCE, GENE THEREOF, AND APPLICATION

(71) Applicant: FEED RESEARCH INSTITUTE, CHINESE ACADEMY OF AGRICULTURAL SCIENCES, Beijing (CN)

(72) Inventors: Huiying Luo, Beijing (CN); Bin Yao, Beijing (CN); Weina Liu, Beijing (CN); Yuan Gu, Beijing (CN); Tao Tu, Beijing (CN); Yuan Wang, Beijing (CN); Yaru Wang, Beijing (CN); Huoqing Huang, Beijing (CN); Yingguo Bai, Beijing (CN); Xiaoyun Su, Beijing (CN); Kun Meng, Beijing (CN)

( * ) Notice: Subject to any disclaimer, the term of this patent is extended or adjusted under 35 U.S.C. 154(b) by 0 days.

(21) Appl. No.: 17/054,526

(22) PCT Filed: May 10, 2019

(86) PCT No.: PCT/CN2019/086348
§ 371 (c)(1),
(2) Date: Nov. 11, 2020

(87) PCT Pub. No.: WO2019/214702
PCT Pub. Date: Nov. 14, 2019

(65) Prior Publication Data
US 2021/0189366 A1   Jun. 24, 2021

(30) Foreign Application Priority Data
May 11, 2018 (CN) .......................... 201810448554.6

(51) Int. Cl.
| | | |
|---|---|---|
| A61K 38/47 | (2006.01) | |
| C12N 9/24 | (2006.01) | |
| C07K 1/14 | (2006.01) | |
| C12N 15/63 | (2006.01) | |

(52) U.S. Cl.
CPC .............. *C12N 9/2491* (2013.01); *C07K 1/14* (2013.01); *C12N 15/63* (2013.01); *C12Y 302/01025* (2013.01)

(58) Field of Classification Search
None
See application file for complete search history.

(56) References Cited

U.S. PATENT DOCUMENTS 10,463,711 B2 * 11/2019 Hamill ...................... A23L 2/66
2021/0189366 A1 * 6/2021 Luo ...................... C12N 9/2491

* cited by examiner

*Primary Examiner* — Hope A Robinson
(74) *Attorney, Agent, or Firm* — Patshegen IP LLC; Moshe Pinchas

(57) ABSTRACT

The present invention relates to a mannanase PMan5A mutant having improved heat resistance, a gene encoding the mutant and application thereof. The mutant is obtained by a substitution of histidine with tyrosine at amino acid residue 93, phenylalanine with tyrosine at amino acid residue 94, leucine with histidine at amino acid residue 356, and/or alanine with proline at amino acid residue 389. The thermal tolerance of the single site mutation mutant H93Y, L356H and A389P are greatly improved over that of the wild-type mannanase PMan5A, and the thermal tolerance of the combination mutants shows the stack effect of the single site mutation, demonstrating the amino acids at the sites of 93, 94, 356, and 389 play an important role for the thermal stability of the mannanase of GH5 family.

Figure 1:
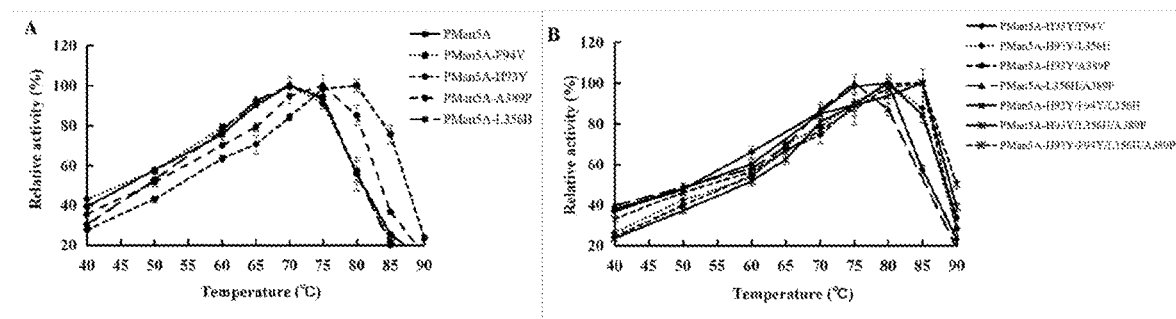

3 Claims, 2 Drawing Sheets
Specification includes a Sequence Listing.

SEQUENCE LISTING

<160> NUMBER OF SEQ ID NOS: 21

<210> SEQ ID NO 1
<211> LENGTH: 435
<212> TYPE: PRT
<213> ORGANISM: Penicillium aculeatum

<400> SEQUENCE: 1

```
Met Lys Ser Ala Ile Leu Ile Leu Pro Phe Leu Ser His Leu Ala Val
1               5                   10                  15

Ser Gln Thr Ala Asn Trp Gly Gln Cys Gly Gly Glu Asn Trp Asn Gly
            20                  25                  30

Asp Thr Thr Cys Asn Pro Gly Trp Tyr Cys Ser Tyr Leu Asn Pro Trp
        35                  40                  45

Tyr Ser Gln Cys Val Pro Gly Ser Gly Ser Ser Ser Ser Thr Thr
    50                  55                  60

Leu Ser Thr Val Val Ser Ser Gln Thr Ser Ser Ile Arg Thr Thr Ser
65                  70                  75                  80

Ala Thr Ser Thr Leu Ala Ala Ser Ala Ser Thr Thr Ala Gly Ser Leu
                85                  90                  95

Pro Ser Ala Ser Gly Thr Ser Phe Val Ile Asp Gly Lys Lys Gly Tyr
            100                 105                 110

Phe Ala Gly Thr Asn Ser Tyr Trp Leu Pro Phe Leu Thr Asn Asn Ala
        115                 120                 125

Asp Val Asp Leu Val Met Gly His Leu Gln Gln Ser Gly Leu Lys Ile
    130                 135                 140

Leu Arg Val Trp Gly Phe Asn Asp Val Asn Ala Val Pro Ser Ser Asp
145                 150                 155                 160

Thr Val Trp Phe Gln Leu Leu Ala Asn Gly Gln Gln Thr Ile Asn Thr
                165                 170                 175

Gly Ser Asp Gly Leu Gln Arg Leu Asp Tyr Val Val Lys Ser Ala Glu
            180                 185                 190

Ala His Gly Ile Lys Leu Ile Ile Asn Phe Val Asn Asn Trp Asp Asp
        195                 200                 205

Phe Gly Gly Met Asn Ala Tyr Val Gln Asn Tyr Gly Asn Gln Thr
    210                 215                 220

Ser Trp Tyr Thr Asn Asn Ala Ala Gln Asp Ala Tyr Lys Thr Tyr Ile
225                 230                 235                 240

Lys Thr Val Ile Ser Arg Tyr Ile Gly Ser Ser Ala Ile Phe Ala Trp
                245                 250                 255

Glu Leu Ala Asn Glu Pro Arg Cys Lys Gly Cys Gly Thr Asp Val Ile
            260                 265                 270

Tyr Asn Trp Ala Gln Ser Thr Ser Gln Tyr Ile Lys Ser Leu Glu Pro
        275                 280                 285

Gly Arg Met Val Cys Ile Gly Asp Glu Gly Met Gly Leu Ser Val Asp
    290                 295                 300

Ser Asp Gly Ser Tyr Pro Phe Gly Tyr Ser Glu Gly Asn Asp Phe Glu
305                 310                 315                 320

Lys Thr Leu Ala Ile Pro Thr Ile Asp Phe Gly Thr Ile His Leu Tyr
                325                 330                 335
```

```
Pro Ser Gln Trp Gly Glu Thr Asp Ser Trp Gly Ser Ser Trp Ile Thr
            340                 345                 350

Ala His Gly Gln Ala Cys Lys Asn Ala Gly Lys Pro Cys Leu Leu Glu
            355                 360                 365

Glu Tyr Gly Ser Thr Ser Leu Cys Ser Ser Glu Ala Pro Trp Gln Thr
        370                 375                 380

Thr Ala Ile Ser Ser Val Ala Ala Asp Leu Phe Trp Gln Trp Gly Asp
385                 390                 395                 400

Thr Leu Ser Thr Gly Gln Ser Ala His Asp Glu Tyr Ser Ile Phe Tyr
                405                 410                 415

Gly Ser Ser Asp Tyr Thr Cys Leu Val Thr Asp His Val Ser Ala Ile
            420                 425                 430

Asp Ser Ala
        435

<210> SEQ ID NO 2
<211> LENGTH: 416
<212> TYPE: PRT
<213> ORGANISM: Penicillium aculeatum

<400> SEQUENCE: 2

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Thr Thr Leu Ser Thr
        35                  40                  45

Val Val Ser Ser Gln Thr Ser Ser Ile Arg Thr Thr Ser Ala Thr Ser
50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly His Phe Ala Gly
            85                  90                  95

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
            115                 120                 125

Trp Gly Phe Asn Asp Val Asn Ala Val Pro Ser Ser Gly Thr Val Trp
            130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
            195                 200                 205

Thr Asn Asn Ala Ala Gln Asp Ala Tyr Lys Tyr Tyr Ile Lys Thr Val
        210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
```

```
            260                 265                 270
Val Cys Ile Gly Asp Glu Gly Met Gly Leu Ser Val Asp Ser Asp Gly
            275                 280                 285

Ser Tyr Pro Phe Gly Tyr Ser Glu Gly Asn Asp Phe Glu Lys Thr Leu
            290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
            340                 345                 350

Ser Thr Ser Leu Cys Ser Ser Glu Ala Pro Trp Gln Thr Thr Ala Ile
            355                 360                 365

Ser Ser Val Ala Ala Asp Leu Phe Trp Gln Trp Gly Asp Thr Leu Ser
            370                 375                 380

Thr Gly Gln Ser Ala His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
                405                 410                 415

<210> SEQ ID NO 3
<211> LENGTH: 416
<212> TYPE: PRT
<213> ORGANISM: Penicillium aculeatum

<400> SEQUENCE: 3

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
            35                  40                  45

Val Val Ser Ser Gln Thr Ser Ser Ile Arg Thr Thr Ser Ala Thr Ser
    50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly Tyr Phe Ala Gly
                85                  90                  95

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
            115                 120                 125

Trp Gly Phe Asn Asp Val Asn Ala Val Pro Ser Ser Gly Thr Val Trp
        130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
            195                 200                 205

Thr Asn Asn Ala Ala Gln Asp Ala Tyr Lys Thr Tyr Ile Lys Thr Val
        210                 215                 220
```

```
Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
            245                 250                 255

Ala Gln Ser Thr Ser Gln Tyr Ile Lys Ser Leu Glu Pro Gly Arg Met
        260                 265                 270

Val Cys Ile Gly Asp Glu Gly Met Gly Leu Ser Val Asp Ser Asp Gly
    275                 280                 285

Ser Tyr Pro Phe Gly Tyr Ser Glu Gly Asn Asp Phe Glu Lys Thr Leu
290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
            325                 330                 335

Gln Ala Cys Lys Asn Ala Gly Lys Pro Cys Leu Leu Glu Glu Tyr Gly
        340                 345                 350

Ser Thr Ser Leu Cys Ser Ser Glu Ala Pro Trp Gln Thr Thr Ala Ile
    355                 360                 365

Ser Ser Val Ala Ala Asp Leu Phe Trp Gln Trp Gly Asp Thr Leu Ser
370                 375                 380

Thr Gly Gln Ser Ala His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
            405                 410                 415

<210> SEQ ID NO 4
<211> LENGTH: 416
<212> TYPE: PRT
<213> ORGANISM: Penicillium aculeatum

<400> SEQUENCE: 4

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
        35                  40                  45

Val Val Ser Ser Gln Thr Ser Ser Ile Arg Thr Thr Ser Ala Thr Ser
    50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly His Tyr Ala Gly
                85                  90                  95

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
        115                 120                 125

Trp Gly Phe Asn Asp Val Asn Ala Val Pro Ser Ser Gly Thr Val Trp
    130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190
```

```
Met Asn Ala Tyr Val Gln Asn Tyr Gly Gly Asn Gln Thr Ser Trp Tyr
        195                 200                 205

Thr Asn Asn Ala Ala Gln Asp Ala Tyr Lys Thr Tyr Ile Lys Thr Val
    210                 215                 220

Ile Ser Arg Tyr Ile Gly Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
            260                 265                 270

Val Cys Ile Gly Asp Glu Gly Met Gly Leu Ser Val Asp Ser Asp Gly
        275                 280                 285

Ser Tyr Pro Phe Gly Tyr Ser Glu Gly Asn Asp Phe Glu Lys Thr Leu
    290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
            340                 345                 350

Ser Thr Ser Leu Cys Ser Ser Glu Ala Pro Trp Gln Thr Thr Ala Ile
        355                 360                 365

Ser Ser Val Ala Ala Asp Leu Phe Trp Gln Trp Gly Asp Thr Leu Ser
370                 375                 380

Thr Gly Gln Ser Ala His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
                405                 410                 415

<210> SEQ ID NO 5
<211> LENGTH: 416
<212> TYPE: PRT
<213> ORGANISM: Penicillium aculeatum

<400> SEQUENCE: 5

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
        35                  40                  45

Val Val Ser Ser Gln Thr Ser Ser Ile Arg Thr Thr Ser Ala Thr Ser
50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly His Phe Ala Gly
                85                  90                  95

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
        115                 120                 125

Trp Gly Phe Asn Asp Val Asn Ala Val Pro Ser Ser Gly Thr Val Trp
130                 135                 140

Phe Gln Leu Leu Ala Asn Gly Gln Gln Thr Ile Asn Thr Gly Ser Asp
```

```
                145                 150                 155                 160
        Gly Leu Gln Arg Leu Asp Tyr Val Val Lys Ser Ala Glu Ala His Gly
                        165                 170                 175

Ile Lys Leu Ile Ile Asn Phe Val Asn Asn Trp Asn Asp Tyr Gly Gly
                        180                 185                 190

Met Asn Ala Tyr Val Gln Asn Tyr Gly Gly Asn Gln Thr Ser Trp Tyr
                        195                 200                 205

Thr Asn Asn Ala Ala Gln Asp Ala Tyr Lys Thr Tyr Ile Lys Thr Val
                        210                 215                 220

Ile Ser Arg Tyr Ile Gly Ser Ser Ala Ile Phe Ala Trp Glu Leu Ala
        225                 230                 235                 240

Asn Glu Pro Arg Cys Lys Gly Cys Gly Thr Asp Val Ile Tyr Asn Trp
                        245                 250                 255

Ala Gln Ser Thr Ser Gln Tyr Ile Lys Ser Leu Glu Pro Gly Arg Met
                        260                 265                 270

Val Cys Ile Gly Asp Glu Gly Met Gly Leu Ser Val Asp Ser Asp Gly
                        275                 280                 285

Ser Tyr Pro Phe Gly Tyr Ser Glu Gly Asn Asp Phe Glu Lys Thr Leu
                        290                 295                 300

Ala Ile Pro Thr Ile Asp Phe Gly Thr Ile His Leu Tyr Pro Ser Gln
        305                 310                 315                 320

Trp Gly Glu Thr Asp Ser Trp Gly Ser Ser Trp Ile Thr Ala His Gly
                        325                 330                 335

Gln Ala Cys Lys Asn Ala Gly Lys Pro Cys Leu Leu Glu Glu Tyr Gly
                        340                 345                 350

Ser Thr Ser His Cys Ser Ser Glu Ala Pro Trp Gln Thr Thr Ala Ile
                        355                 360                 365

Ser Ser Val Ala Ala Asp Leu Phe Trp Gln Trp Gly Asp Thr Leu Ser
                        370                 375                 380

Thr Gly Gln Ser Ala His Asp Glu Tyr Ser Ile Phe Tyr Gly Ser Ser
        385                 390                 395                 400

Asp Tyr Thr Cys Leu Val Thr Asp His Val Ser Ala Ile Asp Ser Ala
                        405                 410                 415

<210> SEQ ID NO 6
<211> LENGTH: 416
<212> TYPE: PRT
<213> ORGANISM: Penicillium aculeatum

<400> SEQUENCE: 6

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
                20                  25                  30

Cys Val Pro Gly Ser Gly Ser Ser Ser Ser Thr Thr Leu Ser Thr
                35                  40                  45

Val Val Ser Ser Gln Thr Ser Ser Ile Arg Thr Thr Ser Ala Thr Ser
        50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly His Phe Ala Gly
                        85                  90                  95

Thr Asn Ser Tyr Trp Leu Pro Phe Leu Thr Asn Asn Ala Asp Val Asp
                100                 105                 110
```

Leu Val Met Gly His Leu Gln Gln Ser Gly Leu Lys Ile Leu Arg Val
            115                 120                 125

Trp Gly Phe Asn Asp Val Asn Ala Val Pro Ser Ser Gly Thr Val Trp
            130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
            195                 200                 205

Thr Asn Asn Ala Ala Gln Asp Ala Tyr Lys Thr Tyr Ile Lys Thr Val
210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
            260                 265                 270

Val Cys Ile Gly Asp Glu Gly Met Gly Leu Ser Val Asp Ser Asp Gly
            275                 280                 285

Ser Tyr Pro Phe Gly Tyr Ser Glu Gly Asn Asp Phe Glu Lys Thr Leu
            290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
            340                 345                 350

Ser Thr Ser Leu Cys Ser Ser Glu Ala Pro Trp Gln Thr Thr Ala Ile
            355                 360                 365

Ser Ser Val Ala Ala Asp Leu Phe Trp Gln Trp Gly Asp Thr Leu Ser
370                 375                 380

Thr Gly Gln Ser Pro His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
                405                 410                 415

<210> SEQ ID NO 7
<211> LENGTH: 416
<212> TYPE: PRT
<213> ORGANISM: Penicillium aculeatum

<400> SEQUENCE: 7

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
            35                  40                  45

Val Val Ser Ser Gln Thr Ser Ser Ile Arg Thr Thr Ser Ala Thr Ser
50                  55                  60

Thr Leu Ala Ala Ser Ala Ser Thr Thr Ala Gly Ser Leu Pro Ser Ala
65                  70                  75                  80

```
Ser Gly Thr Ser Phe Val Ile Asp Gly Lys Lys Gly Tyr Tyr Ala Gly
                85                  90                  95

Thr Asn Ser Tyr Trp Leu Pro Phe Leu Thr Asn Asn Ala Asp Val Asp
           100                 105                 110

Leu Val Met Gly His Leu Gln Gln Ser Gly Leu Lys Ile Leu Arg Val
       115                 120                 125

Trp Gly Phe Asn Asp Val Asn Ala Val Pro Ser Ser Gly Thr Val Trp
   130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
               165                 170                 175

Ile Lys Leu Ile Ile Asn Phe Val Asn Asn Trp Asn Asp Tyr Gly Gly
           180                 185                 190

Met Asn Ala Tyr Val Gln Asn Tyr Gly Gly Asn Gln Thr Ser Trp Tyr
       195                 200                 205

Thr Asn Asn Ala Ala Gln Asp Ala Tyr Lys Thr Tyr Ile Lys Thr Val
   210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
               245                 250                 255

Ala Gln Ser Thr Ser Gln Tyr Ile Lys Ser Leu Glu Pro Gly Arg Met
           260                 265                 270

Val Cys Ile Gly Asp Glu Gly Met Gly Leu Ser Val Asp Ser Asp Gly
       275                 280                 285

Ser Tyr Pro Phe Gly Tyr Ser Glu Gly Asn Asp Phe Glu Lys Thr Leu
   290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
               325                 330                 335

Gln Ala Cys Lys Asn Ala Gly Lys Pro Cys Leu Leu Glu Glu Tyr Gly
           340                 345                 350

Ser Thr Ser Leu Cys Ser Ser Glu Ala Pro Trp Gln Thr Thr Ala Ile
       355                 360                 365

Ser Ser Val Ala Ala Asp Leu Phe Trp Gln Trp Gly Asp Thr Leu Ser
   370                 375                 380

Thr Gly Gln Ser Ala His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
               405                 410                 415
```

<210> SEQ ID NO 8
<211> LENGTH: 416
<212> TYPE: PRT
<213> ORGANISM: Penicillium aculeatum

<400> SEQUENCE: 8

```
Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
           20                  25                  30

Cys Val Pro Gly Ser Gly Ser Ser Ser Ser Ser Thr Thr Leu Ser Thr
```

35                  40                  45
Val Val Ser Ser Gln Thr Ser Ser Ile Arg Thr Thr Ser Ala Thr Ser
 50                  55                  60

Thr Leu Ala Ala Ser Ala Ser Thr Thr Ala Gly Ser Leu Pro Ser Ala
 65                  70                  75                  80

Ser Gly Thr Ser Phe Val Ile Asp Gly Lys Lys Gly Tyr Phe Ala Gly
                 85                  90                  95

Thr Asn Ser Tyr Trp Leu Pro Phe Leu Thr Asn Asn Ala Asp Val Asp
                100                 105                 110

Leu Val Met Gly His Leu Gln Gln Ser Gly Leu Lys Ile Leu Arg Val
                115                 120                 125

Trp Gly Phe Asn Asp Val Asn Ala Val Pro Ser Ser Gly Thr Val Trp
                130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
                180                 185                 190

Met Asn Ala Tyr Val Gln Asn Tyr Gly Gly Asn Gln Thr Ser Trp Tyr
                195                 200                 205

Thr Asn Asn Ala Ala Gln Asp Ala Tyr Lys Thr Tyr Ile Lys Thr Val
210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
                260                 265                 270

Val Cys Ile Gly Asp Glu Gly Met Gly Leu Ser Val Asp Ser Asp Gly
                275                 280                 285

Ser Tyr Pro Phe Gly Tyr Ser Glu Gly Asn Asp Phe Glu Lys Thr Leu
290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
                340                 345                 350

Ser Thr Ser His Cys Ser Ser Glu Ala Pro Trp Gln Thr Thr Ala Ile
                355                 360                 365

Ser Ser Val Ala Ala Asp Leu Phe Trp Gln Trp Gly Asp Thr Leu Ser
                370                 375                 380

Thr Gly Gln Ser Ala His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
                405                 410                 415

<210> SEQ ID NO 9
<211> LENGTH: 416
<212> TYPE: PRT
<213> ORGANISM: Penicillium aculeatum

<400> SEQUENCE: 9

```
Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
            35                  40                  45

Val Val Ser Ser Gln Thr Ser Ser Ile Arg Thr Thr Ser Ala Thr Ser
50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly Tyr Phe Ala Gly
                85                  90                  95

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
            115                 120                 125

Trp Gly Phe Asn Asp Val Asn Ala Val Pro Ser Ser Gly Thr Val Trp
            130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
            165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
            195                 200                 205

Thr Asn Asn Ala Ala Gln Asp Ala Tyr Lys Thr Tyr Ile Lys Thr Val
            210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
            245                 250                 255

Ala Gln Ser Thr Ser Gln Tyr Ile Lys Ser Leu Glu Pro Gly Arg Met
            260                 265                 270

Val Cys Ile Gly Asp Glu Gly Met Gly Leu Ser Val Asp Ser Asp Gly
            275                 280                 285

Ser Tyr Pro Phe Gly Tyr Ser Glu Gly Asn Asp Phe Glu Lys Thr Leu
            290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
            325                 330                 335

Gln Ala Cys Lys Asn Ala Gly Lys Pro Cys Leu Leu Glu Glu Tyr Gly
            340                 345                 350

Ser Thr Ser Leu Cys Ser Ser Glu Ala Pro Trp Gln Thr Thr Ala Ile
            355                 360                 365

Ser Ser Val Ala Ala Asp Leu Phe Trp Gln Trp Gly Asp Thr Leu Ser
            370                 375                 380

Thr Gly Gln Ser Pro His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
            405                 410                 415
```

```
<210> SEQ ID NO 10
<211> LENGTH: 416
<212> TYPE: PRT
<213> ORGANISM: Penicillium aculeatum

<400> SEQUENCE: 10
```

| | | | | | | | | | | | | | | | |
|---|---|---|---|---|---|---|---|---|---|---|---|---|---|---|---|
| Ala | Asn | Trp | Gly | Gln | Cys | Gly | Gly | Glu | Asn | Trp | Asn | Gly | Asp | Thr | Thr |
| 1 | | | | 5 | | | | | 10 | | | | | 15 | |
| Cys | Asn | Pro | Gly | Trp | Tyr | Cys | Ser | Tyr | Leu | Asn | Pro | Trp | Tyr | Ser | Gln |
| | | | 20 | | | | | 25 | | | | | 30 | | |
| Cys | Val | Pro | Gly | Ser | Gly | Ser | Ser | Ser | Ser | Thr | Thr | Leu | Ser | Thr | |
| | | | 35 | | | | | 40 | | | | | 45 | | |
| Val | Val | Ser | Ser | Gln | Thr | Ser | Ser | Ile | Arg | Thr | Thr | Ser | Ala | Thr | Ser |
| | 50 | | | | | 55 | | | | | 60 | | | | |
| Thr | Leu | Ala | Ala | Ser | Ala | Ser | Thr | Thr | Ala | Gly | Ser | Leu | Pro | Ser | Ala |
| 65 | | | | | 70 | | | | | 75 | | | | | 80 |
| Ser | Gly | Thr | Ser | Phe | Val | Ile | Asp | Gly | Lys | Lys | Gly | His | Phe | Ala | Gly |
| | | | | 85 | | | | | 90 | | | | | 95 | |
| Thr | Asn | Ser | Tyr | Trp | Leu | Pro | Phe | Leu | Thr | Asn | Asn | Ala | Asp | Val | Asp |
| | | | 100 | | | | | 105 | | | | | 110 | | |
| Leu | Val | Met | Gly | His | Leu | Gln | Gln | Ser | Gly | Leu | Lys | Ile | Leu | Arg | Val |
| | | | 115 | | | | | 120 | | | | | 125 | | |
| Trp | Gly | Phe | Asn | Asp | Val | Asn | Ala | Val | Pro | Ser | Ser | Gly | Thr | Val | Trp |
| | 130 | | | | | 135 | | | | | 140 | | | | |
| Phe | Gln | Leu | Leu | Ala | Asn | Gly | Gln | Gln | Thr | Ile | Asn | Thr | Gly | Ser | Asp |
| 145 | | | | | 150 | | | | | 155 | | | | | 160 |
| Gly | Leu | Gln | Arg | Leu | Asp | Tyr | Val | Val | Lys | Ser | Ala | Glu | Ala | His | Gly |
| | | | | 165 | | | | | 170 | | | | | 175 | |
| Ile | Lys | Leu | Ile | Ile | Asn | Phe | Val | Asn | Asn | Trp | Asn | Asp | Tyr | Gly | Gly |
| | | | 180 | | | | | 185 | | | | | 190 | | |
| Met | Asn | Ala | Tyr | Val | Gln | Asn | Tyr | Gly | Gly | Asn | Gln | Thr | Ser | Trp | Tyr |
| | | | 195 | | | | | 200 | | | | | 205 | | |
| Thr | Asn | Asn | Ala | Ala | Gln | Asp | Ala | Tyr | Lys | Thr | Tyr | Ile | Lys | Thr | Val |
| | 210 | | | | | 215 | | | | | 220 | | | | |
| Ile | Ser | Arg | Tyr | Ile | Gly | Ser | Ser | Ala | Ile | Phe | Ala | Trp | Glu | Leu | Ala |
| 225 | | | | | 230 | | | | | 235 | | | | | 240 |
| Asn | Glu | Pro | Arg | Cys | Lys | Gly | Cys | Gly | Thr | Asp | Val | Ile | Tyr | Asn | Trp |
| | | | | 245 | | | | | 250 | | | | | 255 | |
| Ala | Gln | Ser | Thr | Ser | Gln | Tyr | Ile | Lys | Ser | Leu | Glu | Pro | Gly | Arg | Met |
| | | | 260 | | | | | 265 | | | | | 270 | | |
| Val | Cys | Ile | Gly | Asp | Glu | Gly | Met | Gly | Leu | Ser | Val | Asp | Ser | Asp | Gly |
| | | | 275 | | | | | 280 | | | | | 285 | | |
| Ser | Tyr | Pro | Phe | Gly | Tyr | Ser | Glu | Gly | Asn | Asp | Phe | Glu | Lys | Thr | Leu |
| | 290 | | | | | 295 | | | | | 300 | | | | |
| Ala | Ile | Pro | Thr | Ile | Asp | Phe | Gly | Thr | Ile | His | Leu | Tyr | Pro | Ser | Gln |
| 305 | | | | | 310 | | | | | 315 | | | | | 320 |
| Trp | Gly | Glu | Thr | Asp | Ser | Trp | Gly | Ser | Ser | Trp | Ile | Thr | Ala | His | Gly |
| | | | | 325 | | | | | 330 | | | | | 335 | |
| Gln | Ala | Cys | Lys | Asn | Ala | Gly | Lys | Pro | Cys | Leu | Leu | Glu | Glu | Tyr | Gly |
| | | | 340 | | | | | 345 | | | | | 350 | | |
| Ser | Thr | Ser | His | Cys | Ser | Ser | Glu | Ala | Pro | Trp | Gln | Thr | Thr | Ala | Ile |
| | | | 355 | | | | | 360 | | | | | 365 | | |
| Ser | Ser | Val | Ala | Ala | Asp | Leu | Phe | Trp | Gln | Trp | Gly | Asp | Thr | Leu | Ser |
| | 370 | | | | | 375 | | | | | 380 | | | | |

```
Thr Gly Gln Ser Pro His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
            405                 410                 415

<210> SEQ ID NO 11
<211> LENGTH: 416
<212> TYPE: PRT
<213> ORGANISM: Penicillium aculeatum

<400> SEQUENCE: 11

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
        35                  40                  45

Val Val Ser Ser Gln Thr Ser Ser Ile Arg Thr Thr Ser Ala Thr Ser
50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Gly Tyr Tyr Ala Gly
                85                  90                  95  Gly

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
        115                 120                 125

Trp Gly Phe Asn Asp Val Asn Ala Val Pro Ser Ser Gly Thr Val Trp
130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
        195                 200                 205

Thr Asn Asn Ala Ala Gln Asp Ala Tyr Lys Thr Tyr Ile Lys Thr Val
210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
            260                 265                 270

Val Cys Ile Gly Asp Glu Gly Met Gly Leu Ser Val Asp Ser Asp Gly
        275                 280                 285

Ser Tyr Pro Phe Gly Tyr Ser Glu Gly Asn Asp Phe Glu Lys Thr Leu
290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
            340                 345                 350
```

Ser Thr Ser His Cys Ser Ser Glu Ala Pro Trp Gln Thr Ala Ile
            355                 360                 365

Ser Ser Val Ala Ala Asp Leu Phe Trp Gln Trp Gly Asp Thr Leu Ser
370                 375                 380

Thr Gly Gln Ser Ala His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
            405                 410                 415

<210> SEQ ID NO 12
<211> LENGTH: 416
<212> TYPE: PRT
<213> ORGANISM: Penicillium aculeatum

<400> SEQUENCE: 12

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
            20                  25                  30

Cys Val Pro Gly Ser Gly Ser Ser Ser Ser Thr Thr Leu Ser Thr
        35                  40                  45

Val Val Ser Ser Gln Thr Ser Ser Ile Arg Thr Thr Ser Ala Thr Ser
50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly Tyr Phe Ala Gly
                85                  90                  95

Thr Asn Ser Tyr Trp Leu Pro Phe Leu Thr Asn Asn Ala Asp Val Asp
            100                 105                 110

Leu Val Met Gly His Leu Gln Gln Ser Gly Leu Lys Ile Leu Arg Val
        115                 120                 125

Trp Gly Phe Asn Asp Val Asn Ala Val Pro Ser Ser Gly Thr Val Trp
130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
        195                 200                 205

Thr Asn Asn Ala Ala Gln Asp Ala Tyr Lys Thr Tyr Ile Lys Thr Val
210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
            260                 265                 270

Val Cys Ile Gly Asp Glu Gly Met Gly Leu Ser Val Asp Ser Asp Gly
        275                 280                 285

Ser Tyr Pro Phe Gly Tyr Ser Glu Gly Asn Asp Phe Glu Lys Thr Leu
290                 295                 300

Ala Ile Pro Thr Ile Asp Phe Gly Thr Ile His Leu Tyr Pro Ser Gln

```
            305                 310                 315                 320
Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
                340                 345                 350

Ser Thr Ser His Cys Ser Ser Glu Ala Pro Trp Gln Thr Thr Ala Ile
                355                 360                 365

Ser Ser Val Ala Ala Asp Leu Phe Trp Gln Trp Gly Asp Thr Leu Ser
            370                 375                 380

Thr Gly Gln Ser Pro His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
                405                 410                 415

<210> SEQ ID NO 13
<211> LENGTH: 416
<212> TYPE: PRT
<213> ORGANISM: Penicillium aculeatum

<400> SEQUENCE: 13

Ala Asn Trp Gly Gln Cys Gly Gly Glu Asn Trp Asn Gly Asp Thr Thr
1               5                   10                  15

Cys Asn Pro Gly Trp Tyr Cys Ser Tyr Leu Asn Pro Trp Tyr Ser Gln
                20                  25                  30

Cys Val Pro Gly Ser Gly Ser Ser Ser Ser Thr Thr Leu Ser Thr
                35                  40                  45

Val Val Ser Ser Gln Thr Ser Ser Ile Arg Thr Thr Ser Ala Thr Ser
            50                  55                  60

Thr Leu Ala Ala Ser Ala Ser Thr Thr Ala Gly Ser Leu Pro Ser Ala
65                  70                  75                  80

Ser Gly Thr Ser Phe Val Ile Asp Gly Lys Lys Gly Tyr Tyr Ala Gly
                85                  90                  95

Thr Asn Ser Tyr Trp Leu Pro Phe Leu Thr Asn Asn Ala Asp Val Asp
                100                 105                 110

Leu Val Met Gly His Leu Gln Gln Ser Gly Leu Lys Ile Leu Arg Val
            115                 120                 125

Trp Gly Phe Asn Asp Val Asn Ala Val Pro Ser Ser Gly Thr Val Trp
130                 135                 140

Phe Gln Leu Leu Ala Asn Gly Gln Gln Thr Ile Asn Thr Gly Ser Asp
145                 150                 155                 160

Gly Leu Gln Arg Leu Asp Tyr Val Val Lys Ser Ala Glu Ala His Gly
                165                 170                 175

Ile Lys Leu Ile Ile Asn Phe Val Asn Asn Trp Asn Asp Tyr Gly Gly
            180                 185                 190

Met Asn Ala Tyr Val Gln Asn Tyr Gly Gly Asn Gln Thr Ser Trp Tyr
            195                 200                 205

Thr Asn Asn Ala Ala Gln Asp Ala Tyr Lys Thr Tyr Ile Lys Thr Val
            210                 215                 220

Ile Ser Arg Tyr Ile Gly Ser Ser Ala Ile Phe Ala Trp Glu Leu Ala
225                 230                 235                 240

Asn Glu Pro Arg Cys Lys Gly Cys Gly Thr Asp Val Ile Tyr Asn Trp
                245                 250                 255

Ala Gln Ser Thr Ser Gln Tyr Ile Lys Ser Leu Glu Pro Gly Arg Met
            260                 265                 270
```

```
Val Cys Ile Gly Asp Glu Gly Met Gly Leu Ser Val Asp Ser Asp Gly
            275                 280                 285

Ser Tyr Pro Phe Gly Tyr Ser Glu Gly Asn Asp Phe Glu Lys Thr Leu
        290                 295                 300

Ala Ile Pro Thr Ile Asp Phe Gly Thr Ile His Leu Tyr Pro Ser Gln
305                 310                 315                 320

Trp Gly Glu Thr Asp Ser Trp Gly Ser Ser Trp Ile Thr Ala His Gly
                325                 330                 335

Gln Ala Cys Lys Asn Ala Gly Lys Pro Cys Leu Leu Glu Glu Tyr Gly
            340                 345                 350

Ser Thr Ser His Cys Ser Ser Glu Ala Pro Trp Gln Thr Thr Ala Ile
        355                 360                 365

Ser Ser Val Ala Ala Asp Leu Phe Trp Gln Trp Gly Asp Thr Leu Ser
370                 375                 380

Thr Gly Gln Ser Pro His Asp Glu Tyr Ser Ile Phe Tyr Gly Ser Ser
385                 390                 395                 400

Asp Tyr Thr Cys Leu Val Thr Asp His Val Ser Ala Ile Asp Ser Ala
                405                 410                 415
```

<210> SEQ ID NO 14
<211> LENGTH: 26
<212> TYPE: DNA
<213> ORGANISM: Artificial Sequence
<220> FEATURE:
<223> OTHER INFORMATION: synthesized primer

<400> SEQUENCE: 14
gacggtaaaa aggggtactt tgctgg                                          26

<210> SEQ ID NO 15
<211> LENGTH: 26
<212> TYPE: DNA
<213> ORGANISM: Artificial Sequence
<220> FEATURE:
<223> OTHER INFORMATION: synthesized primer

<400> SEQUENCE: 15
accccttttt accgtcaatc acgaag                                          26

<210> SEQ ID NO 16
<211> LENGTH: 26
<212> TYPE: DNA
<213> ORGANISM: Artificial Sequence
<220> FEATURE:
<223> OTHER INFORMATION: synthesized primer

<400> SEQUENCE: 16
gtaaaaaggg gcactatgct ggtaca                                          26

<210> SEQ ID NO 17
<211> LENGTH: 27
<212> TYPE: DNA
<213> ORGANISM: Artificial Sequence
<220> FEATURE:
<223> OTHER INFORMATION: synthesized primer

<400> SEQUENCE: 17
tagtgcccct ttttaccgtc aatcacg                                         27

<210> SEQ ID NO 18
<211> LENGTH: 28
<212> TYPE: DNA

```
<213> ORGANISM: Artificial Sequence
<220> FEATURE:
<223> OTHER INFORMATION: synthesized primer

<400> SEQUENCE: 18
gtatggttca actagtcact gtagctcc                                              28

<210> SEQ ID NO 19
<211> LENGTH: 28
<212> TYPE: DNA
<213> ORGANISM: Artificial Sequence
<220> FEATURE:
<223> OTHER INFORMATION: synthesized primer

<400> SEQUENCE: 19
tgactagttg aaccatactc ttcgagga                                              28

<210> SEQ ID NO 20
<211> LENGTH: 29
<212> TYPE: DNA
<213> ORGANISM: Artificial Sequence
<220> FEATURE:
<223> OTHER INFORMATION: synthesized primer

<400> SEQUENCE: 20
gagtactgga cagtctccgc atgacgagt                                             29

<210> SEQ ID NO 21
<211> LENGTH: 29
<212> TYPE: DNA
<213> ORGANISM: Artificial Sequence
<220> FEATURE:
<223> OTHER INFORMATION: synthesized primer

<400> SEQUENCE: 21
cggagactgt ccagtactca atgtatcac                                             29
```

MANNANASE PMAN5A MUTANT HAVING IMPROVED HEAT RESISTANCE, GENE THEREOF, AND APPLICATION

CROSS REFERENCE TO RELATED APPLICATIONS

This application claims priority to China Application No. 201810448554.6, filed May 11, 2018.

FIELD OF THE INVENTION

The present invention relates to the field of genetic engineering, particularly to mannanases PMAN5A mutant having improved heat resistance, gene and application thereof.

BACKGROUND OF THE INVENTION

Mannan is the major component of plant hemicellulose, which mainly exists in phellem plants and the special structures such as plant seeds. It is also an important plant feedstuff. The mannan has the complex structure, comprising the main chain of a linear polysaccharide linked by 1,4-β-D-mannopyranoside bond, and the side chain which are substituted by the different groups. The complete hydrolysis of mannan requires the cooperation of many enzymes including endo-β-mannanase, exo-β-mannosidase, β-glucosidase, acetyl mannanase and α-galactosidase due to its diversity and structural complexity, wherein the endo-β-mannanase can degrade the β-1,4-glycosidic bonds in the main chain of the mannan, which is the most important enzyme in the degradation of the mannan.

The prior endo-β-mannanases can be divided into the families of GH5, 26,113 or 134 according to the classification of glycoside hydrolase family, wherein there are many reports about GH5 family having the limited application to the various fields due to its poor tolerance to the extreme environment, the low catalytic activity and the weak affinity to substrates, which promotes the development of the novel enzyme genes and the research of the enzyme modification. There are many factors affecting the structure and properties of the β-mannanase, including the hydrogen bond, the salt bridge and the disulfide bond. The thermal stability of protein is related to many structural characteristics.

ORDER OF THE INVENTION

In order to solve the problems of the poor thermal tolerance and the low catalytic activity of the β-mannanase, the present invention obtains the mannanase mutants with improved thermal stability by substituting one or more amino acids H, F, L or A at the sites of 93, 94, 356 and/or 389 of the amino acid sequence of the β-mannanase PMan5A with Y, Y, H or P, respectively.

Therefore, the order of the present invention is to provide the single site mutation, double-sites combination mutation, and multiple-sites combination mutation mannanase mutants.

Another order of the present invention is to provide a gene encoding the above mutants.

Another order of the present invention is to provide a recombinant vector comprising the above gene encoding the above mutants.

Another order of the present invention is to provide a recombinant strain comprising the above gene encoding the above mutants.

Another order of the present invention is to provide a method of preparing the mannanase having improved thermal stability and catalytic activity.

Another order of the present invention is to provide a use of the above mutants.

SUMMARY OF THE INVENTION

According to embodiment of the present invention, the wild mannanase has the amino acid sequence of SEQ ID NO: 1 comprising the signal peptide having 19 amino acids sequence, "MKSAILILPF LSHLAVSQT", at the N-terminal.

```
                                                        SEQ ID NO: 1
  1  MKSAILILPF  LSHLAVSQTA  NWGQCGGENW  NGDTTCNPGW  YCSYLNPWYS

51  QCVPGSGSSS  SSTTLSTVVS  SQTSSIRTTS  ATSTLAASAS  TTAGSLPSAS

101  GTSFVIDGKK  GYFAGTNSYW  LPFLTNNADV  DLVMGHLQQS  GLKILRVWGF

151  NDVNAVPSSD  TVWFQLLANG  QQTINTGSDG  LQRLDYVVKS  AEAHGIKLII

201  NFVNNWDDFG  GMNAYVQNYG  GNQTSWYTNN  AAQDAYKTYI  KTVISRYIGS

251  SAIFAWELAN  EPRCKGCGTD  VIYNWAQSTS  QYIKSLEPGR  MVCIGDEGMG

301  LSVDSDGSYP  FGYSEGNDFE  KTLAIPTIDF  GTIHLYPSQW  GETDSWGSSW

351  ITAHGQACKN  AGKPCLLEEY  GSTSLCSSEA  PWQTTAISSV  AADLFWQWGD

401  TLSTGQSAHD  EYSIFYGSSD  YTCLVTDHVS  AIDSA
```

According to the embodiment of the present invention, the mature mannanase PMan5A having the amino acid sequence of SEQ ID NO: 2 is modified.

```
                                                        SEQ ID NO: 2
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGHFAGTNSY
```

```
101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSLCSSE  APWQTTAISS  VAADLFWQWG  DTLSTGQSAH  DEYSIFYGSS

401  DYTCLVTDHV  SAIDSA
```

In one aspect, the present invention provides mutants by substituting histidine (H) at the site of 93 of the mannanase having the amino sequence of SEQ ID NO: 2 with tyrosine (Y), wherein the obtained mutant H93Y having the amino sequence of SEQ ID NO: 3.

```
                                                  SEQ ID NO: 3
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGYFAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSLCSSE  APWQTTAISS  VAADLFWQWG  DTLSTGQSAH  DEYSIFYGSS

401  DYTCLVTDHV  SAIDSA
```

According to a further embodiment of the present invention, the mannanase having the amino sequence of SEQ ID NO: 2 is mutated at the sites of 94, 356 or 389.

According to a further embodiment of the present invention, the mannanase having the amino sequence of SEQ ID NO: 2 is mutated by substituting phenylalanine (F) at the site of 94 with tyrosine (Y), leucine (L) at the site of 356 with histidine (H), and alanine (A) at the site of 389 with proline (P).

According to the embodiment of the present invention, the mature mannanase is mutated by substituting phenylalanine (F) at the site of 94 with tyrosine (Y) to obtain the mutant F94Y having the amino sequence of SEQ ID NO:4.

```
SEQ ID NO: 4:
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGHYAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSLCSSE  APWQTTAISS  VAADLFWQWG  DTLSTGQSAH  DEYSIFYGSS

401  DYTCLVTDHV  SAIDSA
```

According to embodiment of the present invention, the wild mannanase is mutated by substituting leucine (L) at the site of 356 with histidine (H) to obtain the mutant L356H having the amino sequence of SEQ ID NO:5.

```
SEQ ID NO: 5:
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGHFAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSHCSSE  APWQTTAISS  VAADLFWQWG  DTLSTGQSAH  DEYSIFYGSS

401  DYTCLVTDHV  SAIDSA
```

According to the embodiment of the present invention, the wild mannanase is performed at least one of the substitutions of H93Y, F94Y, L356H or A389P, or the any combination of the above single site substitutions, to obtain the mutants H93Y/L356H, H93Y/A389P, H93Y/F94Y or H93Y/other site; H93Y/F94Y/L356H, H93Y/L356H/A389P, or H93Y/F94Y/A389P, H93Y/F94Y//other site, H93Y/L356H/other site, H93Y/A389P/other site; or H93Y/F94Y/L356H/A389P/other site.

According to embodiment of the present invention, the wild mannanase is mutated by substituting alanine (A) at the site of 389 with proline (P) to obtain the mutant A389P having the amino sequence of SEQ ID NO:6.

```
                                                SEQ ID NO:: 6
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGHFAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSLCSSE  APWQTTAISS  VAADLFWQWG  DTLSTGQSPH  DEYSIFYGSS

401  DYTCLVTDHV  SAIDSA
```

Particularly, according to the embodiment of the present invention, the mannanase is mutated by substituting histidine (H) at the site of 93 with tyrosine (Y), and phenylalanine (F) at the site of 94 with tyrosine (Y) to obtain the mutant H93Y/F94Y having the amino sequence of SEQ ID NO:7.

```
                                                SEQ ID NO: 7
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGYYAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSLCSSE  APWQTTAISS  VAADLFWQWG  DTLSTGQSAH  DEYSIFYGSS

401  DYTCLVTDHV  SAIDSA
```

According to the embodiment of the present invention, the mannanase is mutated by substituting histidine (H) at the site of 93 with tyrosine (Y), and leucine (L) at the site of 356 with histidine (H) to obtain the mutant H93Y/L356H having the amino sequence of SEQ ID NO:8.

```
SEQ ID NO: 8:
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGYFAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSHCSSE  APWQTTAISS  VAADLFWQWG  DTLSTGQSAH  DEYSIFYGSS

401  DYTCLVTDHV  SAIDSA
```

According to the embodiment of the present invention, the mannanase is mutated by substituting histidine (H) at the site of 93 with tyrosine (Y), and alanine (A) at the site of 389 with proline (P) to obtain the mutant H93Y/A389P having the amino sequence of SEQ ID NO:9.

```
SEQ ID NO: 9:
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGYFAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSLCSSE  APWQTTAISS  VAADLFWQWG  DTLSTGQSPH  DEYSIFYGSS

401  DYTCLVTDHV  SAIDSA
```

According to the embodiment of the present invention, the mannanase is mutated by substituting leucine (L) at the site of 356 with histidine (H) and alanine (A) at the site of 389 with proline (P) to obtain the mutant L356H/A389P having the amino sequence of SEQ ID NO:10.

```
                                                   SEQ ID NO: 10
  1  ANWGQCGGEN  WNGDTTCNPG  WYCSYLNPWY  SQCVPGSGSS  SSSTTLSTVV

51  SSQTSSIRTT  SATSTLAASA  STTAGSLPSA  SGTSFVIDGK  KGHFAGTNSY

101  WLPFLTNNAD  VDLVMGHLQQ  SGLKILRVWG  FNDVNAVPSS  GTVWFQLLAN

151  GQQTINTGSD  GLQRLDYVVK  SAEAHGIKLI  INFVNNWNDY  GGMNAYVQNY

201  GGNQTSWYTN  NAAQDAYKTY  IKTVISRYIG  SSAIFAWELA  NEPRCKGCGT

251  DVIYNWAQST  SQYIKSLEPG  RMVCIGDEGM  GLSVDSDGSY  PFGYSEGNDF

301  EKTLAIPTID  FGTIHLYPSQ  WGETDSWGSS  WITAHGQACK  NAGKPCLLEE

351  YGSTSHCSSE  APWQTTAISS  VAADLFWQWG  DTLSTGQSPH  DEYSIFYGSS

401  DYTCLVTDHV  SAIDSA
```

According to the embodiment of the present invention, the mannanase is mutated by substituting histidine (H) at the site of 93 with tyrosine (Y), phenylalanine (F) at the site of 94 with tyrosine (Y), and leucine (L) at the site of 356 with histidine (H) to obtain the mutant H93Y/F94Y/L356H having the amino sequence of SEQ ID NO:11.

```
                                             SEQ ID NO: 11
  1   ANWGQCGGEN WNGDTTCNPG WYCSYLNPWY SQCVPGSGSS SSSTTLSTVV

51   SSQTSSIRTT SATSTLAASA STTAGSLPSA SGTSFVIDGK KGYYAGTNSY

101   WLPFLTNNAD VDLVMGHLQQ SGLKILRVWG FNDVNAVPSS GTVWFQLLAN

151   GQQTINTGSD GLQRLDYVVK SAEAHGIKLI INFVNNWNDY GGMNAYVQNY

201   GGNQTSWYTN NAAQDAYKTY IKTVISRYIG SSAIFAWELA NEPRCKGCGT

251   DVIYNWAQST SQYIKSLEPG RMVCIGDEGM GLSVDSDGSY PFGYSEGNDF

301   EKTLAIPTID FGTIHLYPSQ WGETDSWGSS WITAHGQACK NAGKPCLLEE

351   YGSTSHCSSE APWQTTAISS VAADLFWQWG DTLSTGQSAH DEYSIFYGSS

401   DYTCLVTDHV SAIDSA
```

According to the embodiment of the present invention, the mannanase is mutated by substituting histidine (H) at the site of 93 with tyrosine (Y), and leucine (L) at the site of 356 with histidine (H), and alanine (A) at the site of 389 with proline (P) to obtain the mutant H93Y/L356H/A389P having the amino sequence of SEQ ID NO:12.

```
                                             SEQ ID NO: 12
  1   ANWGQCGGEN WNGDTTCNPG WYCSYLNPWY SQCVPGSGSS SSSTTLSTVV

51   SSQTSSIRTT SATSTLAASA STTAGSLPSA SGTSFVIDGK KGYFAGTNSY

101   WLPFLTNNAD VDLVMGHLQQ SGLKILRVWG FNDVNAVPSS GTVWFQLLAN

151   GQQTINTGSD GLQRLDYVVK SAEAHGIKLI INFVNNWNDY GGMNAYVQNY

201   GGNQTSWYTN NAAQDAYKTY IKTVISRYIG SSAIFAWELA NEPRCKGCGT

251   DVIYNWAQST SQYIKSLEPG RMVCIGDEGM GLSVDSDGSY PFGYSEGNDF

301   EKTLAIPTID FGTIHLYPSQ WGETDSWGSS WITAHGQACK NAGKPCLLEE

351   YGSTSHCSSE APWQTTAISS VAADLFWQWG DTLSTGQSPH DEYSIFYGSS

401   DYTCLVTDHV SAIDSA
```

According to the embodiment of the present invention, the mannanase is mutated by substituting histidine (H) at the site of 93 with tyrosine (Y), phenylalanine (F) at the site of 94 with tyrosine (Y), leucine (L) at the site of 356 with histidine (H), and alanine (A) at the site of 389 with proline (P) to obtain the mutant H93Y/F94Y/L356H/A389P having the amino sequence of SEQ ID NO:13.

```
SEQ ID NO: 13:
  1   ANWGQCGGEN WNGDTTCNPG WYCSYLNPWY SQCVPGSGSS SSSTTLSTVV

51   SSQTSSIRTT SATSTLAASA STTAGSLPSA SGTSFVIDGK KGYYAGTNSY

101   WLPFLTNNAD VDLVMGHLQQ SGLKILRVWG FNDVNAVPSS GTVWFQLLAN

151   GQQTINTGSD GLQRLDYVVK SAEAHGIKLI INFVNNWNDY GGMNAYVQNY

201   GGNQTSWYTN NAAQDAYKTY IKTVISRYIG SSAIFAWELA NEPRCKGCGT

251   DVIYNWAQST SQYIKSLEPG RMVCIGDEGM GLSVDSDGSY PFGYSEGNDF
```

```
301  EKTLAIPTID FGTIHLYPSQ WGETDSWGSS WITAHGQACK NAGKPCLLEE

351  YGSTSHCSSE APWQTTAISS VAADLFWQWG DTLSTGQSPH DEYSIFYGSS

401  DYTCLVTDHV SAIDSA
```

In a yet preferred embodiment of the present invention, said mutant is obtained by substitution, deletion and/or insertion of one or more, e.g., 1, 2, 3, 4, 5, 6, 7, 8 or 9, amino acid residues of the polypeptide of SEQ ID NO:3 to 13, and maintaining the properties of the above mannanase mutant. For example, a common strategy is substitutions of the conservative amino acid that the amino acid residue is replaced with another amino acid residue having a similar side chain without effect on the properties of the enzyme. Families of amino acid residues having similar side chains have been defined in the art. Furthermore, it is well known in the art that the suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions of the proteins, in order to construct a fusion protein, to enhance expression of recombinant protein, to obtain an recombinant protein automatically secreted outside the host cell, or to aid in the purification of the recombinant protein.

In another aspect, the present invention provides the gene encoding the above mannanase mutants.

According the embodiment of the present invention, the present invention provides a gene having a nucleotide sequence which hybridizes to a nucleotide sequence encoding the polypeptides of SEQ ID NO:3 to 13 under stringent conditions. As used here, the term "hybridize under stringent conditions" refers to the hybridization and cleaning conditions in which at least 90% of homologous nucleotide sequences can still be hybridized with each other. The said stringent condition are well known to those skilled in the art and can be found in current protocols in molecular biology, John Wiley & Sons, N.Y. (1989), 6.3.1-6.3.6. One example of hybridization under stringent conditions is hybridization in 6×SSC at 45° C., then washing one or more times at 50-65° C. in 0.2×SSc and 0.1% SDS. Those skilled in the art can understand that highly stringent conditions can be achieved by increasing the hybridization temperature, for example, to 50° C., 55° C., 60° C. or 65° C.

In addition, those skilled in the art will understand that there may exist the genetic polymorphism due to natural variation among individuals of a population. The gene encoding the mannanase mutants of the present invention may have such natural variation without changing the activity of the mutant. Therefore, the present invention also includes alleles of a gene encoding a polypeptide having an amino acid sequence of SEQ ID No: 3 to 13.

In another aspect, the present invention provides recombinant vector comprising the gene encoding the abovementioned mannanase mutants. The recombinant expression vectors of the invention can be designed for expressing mannanase in prokaryotic or eukaryotic cells. For example, mannanase can be expressed in bacterial cells such as *E. coli*, yeast such as *Pichia* or *Aspergillus*, insect cells such as Sf9 cell or silkworm cell with baculovirus expression vectors, or plant cell such as *Arabidopsis*, tobacco, corn, and so on, mediated by *Agrobacterium tumefaciens*. Thus, the invention relates to host cells introduced with a recombinant expression vector of the invention. The host cells of the present invention may be any prokaryotic or eukaryotic cell, including but not limited to the above host cells. Preferably, said host cell is *Pichia* preferred. *Pichia pastoris* is methylotrophic yeast, capable of metabolizing methanol as its sole carbon source. This system is well-known for its ability to express high levels of heterologous proteins. As an effective expression system, many of the gene encoding the mannanase have successfully expressed in *P. pastoris*. The novel gene encoding the mutant mannanase of the present invention is also expressed in *P. pastoris* with high levels. So it will be very easy to mass-produce the polygalacturonase by fermentation in the lower cost than ever.

In a preferred embodiment, the vector DNA can be transferred into prokaryotic or eukaryotic cells by the conventional transformation or transfection methods. Appropriate methods for transforming or transfecting host cells can be found in the second edition of *Molecular cloning* (Sambrook et al.), and other laboratory manuals.

In a preferred embodiment, the present invention provides a recombinant strain comprising the above gene encoding the said mutant mannanase.

In another aspect, the present invention provides a method of preparing the mutant mannanase including the step of culturing the host cells transformed by the recombinant vector comprising the gene encoding the above mutants in the culture medium to produce the mannanase.

According to the embodiment of the present invention, said method includes the step of isolating the mannanase from the culture medium.

According to the embodiment of the present invention, said method includes the step of purifying the mannanase by ammonium sulfate precipitation, dialysis, ultrafiltration and chromatography, for researching the properties of the mannanase.

According to the embodiment of the present invention, said method includes the step of
(1) transforming the a host cell with the DNA construct or a recombinant vector of comprising said gene encoding the above mannanase mutants to obtain the recombinant host cell;
(2) cultivating the recombinant host cell to induce the expression of mannanase; and
(3) isolating and recovering said mannanase.

In another aspect, the present invention provides an application of the above mannanase mutants to the fields of feed, food, detergent, biofuel or oil exploitation.

The present invention obtains 11 mutants by performing the single or combined mutation of the $93^{th}$, $94^{th}$, $356^{th}$, and/or $389^{th}$ amino acid of the mature mannanasePman5A, which are transformed to *Pichia pastoris* GS115 to induce the expression of the mutant and the wild mannanase for being detected thermal tolerance and catalytic activity.

The results shows that the enzyme activities of the single-site mutation mutants Pman5A-H93Y and Pman5A-A389P are significantly improved than that of the wild at the high temperature, while the optimum temperatures of the mutants Pman5A-F94Y and the mutant Pman5A-L356H keep unchanged, and show the relative enzyme activities similar to that of the wild mannanasePman5A at the different temperatures. The double-sites combination mutation mutants H93Y/F94Y, H93Y/L356H, H93Y/A389P and L353/A389P have the optimum temperatures increased by 10° C., 10° C., 15° C. and 5° C. compared with that of the wild mannanase respectively, and a synergistic stack effect to increase the optimum temperatures of the mutants. Also, the combination mutation mutants H93/L353/A389P and H93/F94Y/L353/A389P show the same stack effect, and have the optimum temperatures increased to 85° C.

The results show the improvement of the thermal tolerance of the mutants H93Y, L356H and A389P at 70° C., wherein the substitutions of H93 and A389 do more to improve the thermal tolerance. And, compared with that of the wild mannanase, the thermal stability of all of the combination mutation mutants is improved.

The $T_{50}$ values of the single-site mutation mutants H93Y, L356H and nA389P are increased by 7° C., 2° C. and 4° C. respectively compared with that of the wild mannanase, while the $T_{50}$ value of the mutant F94Y doesn't change, demonstrating that this three amino acid sites are the key to improve the thermal stability of GH5 mannanase, and their effects are H93Y>A389P>L356H in rank. And, the combined mutation can generate an obviously stack effect to improve the thermal tolerance of the mannanase, wherein the combination mutation mutants H93Y/F94Y/L356H, H93Y/L356H/A389P and H93Y/F94Y/L356H/A389P show the higher thermal tolerance, and have $T_{50}$ values increased by 10° C., 13° C. and 14° C. compared with that of the wild mannanase, respectively.

All of the thermal tolerance of all the four single-site mutation mutants H93Y, F94Y, L356H and A389P at 70° C. are improved, and the thermal tolerance of the combination mutation mutants are ranked in the order of the mutant L353/A389P L353/A389P<the mutant H93Y/F94Y<the mutant H93Y/F94Y/L356H<the mutant H93Y/A389P<the mutant H93Y/L356H/A389P<the mutant H93Y/F94Y/L356H/A389P, indicating that the combination mutation generates stack effect to improve the thermal tolerance of the mannanase.

The sites of H93 and A389 are important for the thermal stability of the mannanase, providing the stack effect. Although the mutations of F94Y and L356H don't increase the $T_m$ value of the wild enzyme, they showed a superposition of $T_m$ values when combined with other mutation sites.

The catalytic efficiency and specific activity of all the mutants are higher than those of the wild mannanase PMan5A, wherein the improvement of the single-site mutation is lower than that of the double-site mutation, which is lower than that of the multiple-sites mutation, he specific activity and catalytic efficiency of the combination mutation mutants H93Y/F94Y/L356H/A389P are increased by 0.7 times and 0.5 times, respectively.

The present invention proves the importance of the sites of H93, F94, H356 and A389 in the mannanase PMan5A to improvement of the thermal tolerance, and provides an important clue for the studying the thermal stability mechanism of the mannanase PMan5A, and a reliable reference basis for improving the thermal stability of other mannanases of GH5 family.

BRIEF DESCRIPTIONS OF THE DRAWINGS

Figure 2:
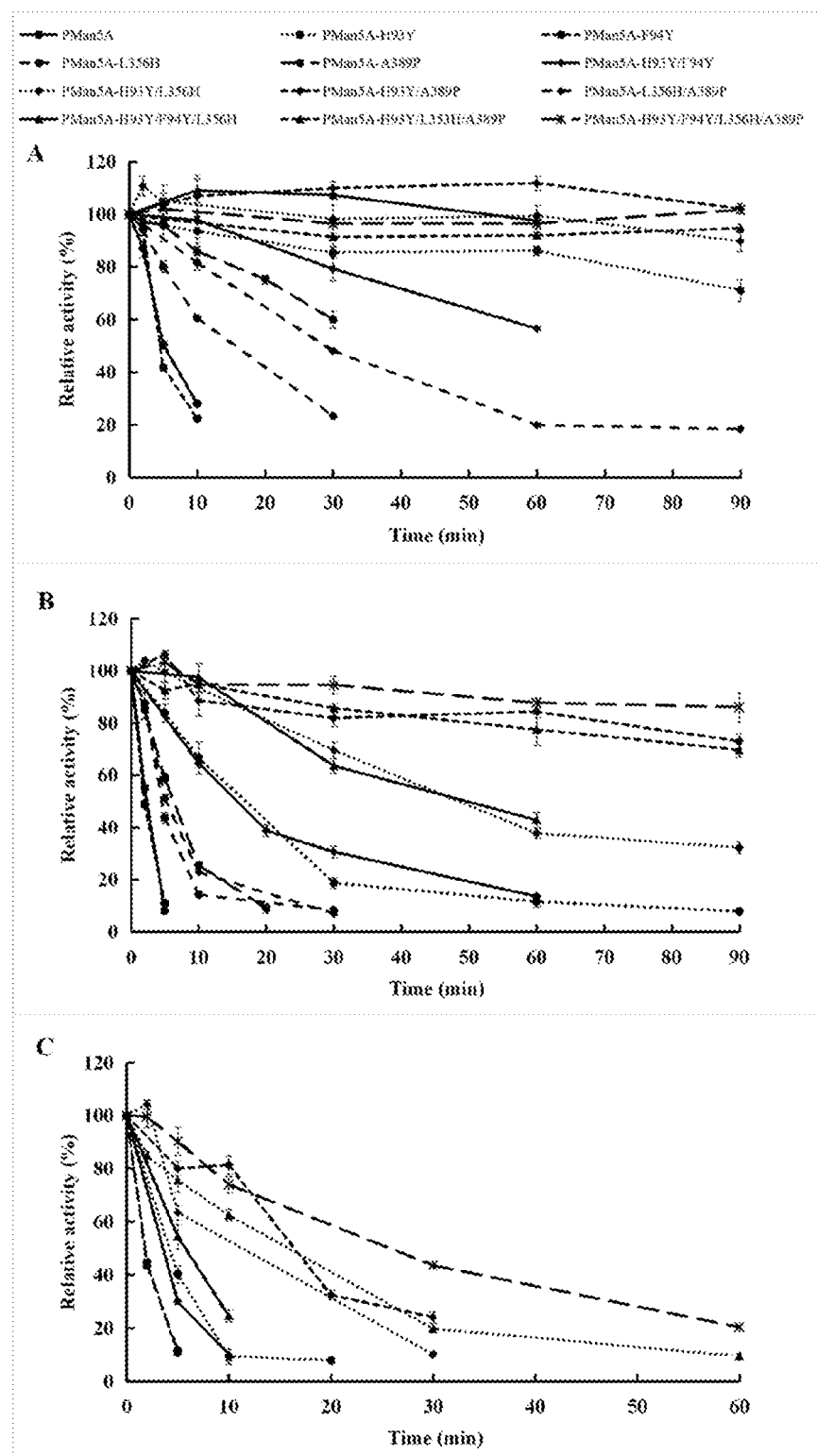

FIG. 1 shows the optimum temperatures of the wild mannanase PMan5A and the mutants, wherein "A" representing the single site mutation mutants, and B representing the combined sites mutation mutants; and FIG. 2 shows thermal stability of the wild mannanase PMan5A and the mutants, wherein "A": 70° C.; "B": 75° C.; C: 80° C.

EMBODIMENT

Test Materials and Reagents
1. Strains and vectors: host: *Pichia pastoris* GS115; and vector pPIC9;
2. Enzymes and other biochemical reagents: Site-Mutation Kit, restriction endonucleases; and ligase.
3. Medium:
(1) *E. coli*. LB medium: 1% of peptone, 0.5% of yeast extract, and 1% of NaCl, natural pH;
(2) YPD medium: 1% of yeast extract, 2% of peptone, and 2% of glucose;
(3) MD solid medium: 2% of glucose, 1.5% of agarose, 1.34% of YNB, and 0.00004% of biotin;
(4) BMGY medium: 1% of yeast extract; 2% of peptone; 1.34% of YNB, 0.00004% of Biotin; and 1% of glycerol(V/V).
(5) BMMY medium: 1% of yeast extract; 2% of peptone; 1.34% of YNB, 0.00004% of Biotin; and 0.5% of methanol (V/V).

Suitable biology laboratory methods not particularly mentioned in the examples as below can be found in Sambrook, et al. (*Molecular Cloning: A Laboratory Manual.* 2nd, ed., Cold Spring Harbor Laboratory, Cold Spring Harbor Laboratory Press, Cold Spring Harbor, N Y, 1989), and other kit laboratory manuals.

Example 1 Constructing the Strain Comprising the Mutant Mannanase (1) Constructing the Expression Vector and Expressing in *Pichia pastoris* GS115

The mutation primers H93Y F/R, F94Y F/R, L356H F/R and A389P F/R (as shown in Table 1) were designed at the sites of H93, F94, L356 and A389, for performing the PCR application using plasmid Pman5A-pPIC9 comprising the mannanase gene from *Penicillium* sp. WN1 as the template with Site-Mutation Kit. The PCR product was demethylated by DMT enzyme and transformed into DMT competent cells, followed by selecting monoclonal cells and verifying the positive transformants by DNA sequencing. The transformants confirmed by sequencing were used to prepare a large number of recombinant plasmids.

TABLE 1

Primers for constructing the mutant of the wild mannanase PMan5A

| Primers | Sequence (5'→3') | Length (bp) |
|---|---|---|
| H93Y F | GACGGTAAAAAGGGGTACTTTGCTGG | 26 |
| H93Y R | ACCCCTTTTTACCGTCAATCACGAAG | 26 |
| F94Y F | GTAAAAAGGGGCACTATGCTGGTACA | 26 |
| F94Y R | TAGTGCCCCTTTTTACCGTCAATCACG | 27 |
| L356H F | GTATGGTTCAACTAGTCACTGTAGCTCC | 28 |
| L356H R | TGACTAGTTGAACCATACTCTTCGAGGA | 28 |

TABLE 1-continued

Primers for constructing the mutant
of the wild mannanase PMan5A

| Primers | Sequence (5'→3') | Length (bp) |
|---|---|---|
| A389P F | GAGTACTGGACAGTCTCCGCATGACGAGT | 29 |
| A389P R | CGGAGACTGTCCAGTACTCAATGTATCAC | 29 |

The recombinant vector that was connected with the expressing vector pPIC9 and confirmed by sequencing was linearized with the endonuclease Dra I and transformed into competent cells of Pichia pastoris GS115, followed by being cultured for 2 to 3 days at 30° C., and selecting the transformants on MD plates for the further expression test to obtain the recombinant yeast strain.

(2) Screening of the Transformants with High Mannanase Activity

The single colony on the MD plate was selected with a sterilized toothpick and numbered on the MD plates which were incubated at 30° C. for 1 to 2 days until the colony grown. The transformants were inoculated in a centrifuge tube containing 3 mL BMGY medium, and cultured according to their number, cultured at 30° C. and 220 RPM for 48 h followed by centrifuging at 3,000×g for 15 min to remove supernatant, and adding 1 mL BMMY medium containing 0.5% of methanol into the centrifuge tube for induction culturing at 30° C. and 220 RPM for 48 h to collect the supernatant by centrifuging at 3,000×g for 5 min for detecting the activity. Finally, the transformant with high glucose oxidase activity were screened out. The particular operation refers to Pichia pastoris expression manual.

Example 2 Preparation of the Mannanase Mutant and Wild Enzyme Fermentation Broth (1) Expression of the Mutant Gene at Shake Flask Level in Pichia pastoris The screened transformant with the highest activity was inoculated in 30 ML of YPD medium for 48 h for seed amplification, followed by being incubated in 300 mL of BMGY for 48 h at 30° C. and 220 rpm, and then being spun down by centrifuging at 3000 rpm for 5 min to remove the supernatant. The obtained precipitate was suspended in 200 mL of BMMY containing 0.5% of methanol to induce the mannanase gene expression at 30° C. and 220 rpm with addition of 1 mL of methanol solution every 12 hours to keep concentration of methanol as 0.5% by compensating the loss of methanol. After induction, the supernatant was recovered by spinning to test the activity of the enzyme.

(2) Purifying the Recombinant Mannanase

The supernatant of the recombinant mannanase expressed in the shaking bottle was collected followed by being concentrated with 10 kDa membrane package while replacing the medium of the fermentation broth with low salt buffer, and further concentrated with 10 kDa ultrafiltration tube. The concentrated solution was further purified with ion exchange chromatography by loading 2.0 mL of the wild mannanase and the mutants concentrate into anion column sold under the trademark HiTrap® Q Sepharose® XL pre-balanced with 10 mMPBS (pH 7.2), and eluting with NaCL in linear gradient of 0 to 1 mol/L, to detect enzyme activity and determine protein concentration of the eluent collected step by step.

Example 3 Measuring the Activity and the Properties of the Recombinant Mannanase The enzymatic activity of mannanase was determined with UV spectrophotometer by the steps of performing the enzymatic reaction at the certain temperature and pH for 10 min, wherein 1 mL of said enzymatic reaction system included 100 µL of appropriate diluted enzyme solution and 900 µL of substrate, adding 1.5 mL of DNS to terminate the reaction, boiling for 5 min, cooling, measuring the absorbance at 540 nm and calculating the enzymatic activity. A unit of enzymatic activity (U) is defined as the amount of enzyme to produce 1 µmol of reducing sugar by decomposing carrageenan per minute under given conditions.

(1) Measuring the Optimum Temperature and Thermal Stability for the Wild and the Mutant Mannanase The wild and the mutant mannanase were reacted in the different temperatures from 40 to 90° C. at pH 5.0 in citric acid disodium hydrogen phosphate buffer system to determine their optimum temperature.

As shown in FIGS. 1 and 2, the optimum temperatures of the single site mutation mutants H93Y, F94Y, L356H and A389P were 80° C., 70° C., 70° C. and 75° C. respectively, wherein the optimum temperatures of the mutants H93Y and A389P were 10° C. and 5° C. higher than that of the wild mannanase respectively, and the mutants F94Y and L356H had the unchanged optimum temperatures and the similar relative enzyme activity to that of the wild mannanase Pman5A at the different temperatures. Thus, the enzyme activities of the single site mutation mutants H93Y and A389P were obviously higher than that of the wild mannanasePman5A.

The optimum temperatures of the double-sites mutation mutant H93Y/F94Y, H93Y/L356H, H93Y/A389P and L353/A389P were 80° C., 80° C., 85° C. and 75° C. which were 10° C., 10° C., 15° C. and 5° C. higher than that of the wild mannanase Pman5A respectively, wherein the optimum temperature of the mutant H93Y/A389P was only increased by 5° C. comparing with that of the single-site mutation mutant H93Y, and the double-sites combination mutation mutants showed the stack effect to the increase of the optimum temperature comparing with the single-site mutation mutants H93Y and A389P.

And, the combination mutation mutants H93/L353/A389P and H93/F94Y/L353/A389P showed the same stack effect, and have the optimum temperatures increased to 85° C.

(2) Measuring $T_m$ Values of the Wild and the Mutant Mannanase 0.25 mg of the protein sample was solved into 1 mL of 10 mM citric acid disodium hydrogen phosphate buffer solution in pH 7.2 to scan at 25 to 100° C. with the scanning speed of 1° C./min. The results were shown in Table 2.

TABLE 2

$T_m$ values of the wild and the mutant mannanase

| variant | $T_m$ (° C.) | Δ $T_m$ (° C.) |
|---|---|---|
| Pman5A | 61.8 ± 0.04 | |
| H93Y | 69.2 ± 0.02 | 7.5 |
| F94Y | 61.8 ± 0.05 | 0.1 |
| L356H | 63.5 ± 0.18 | 1.7 |
| A389P | 66.8 ± 0.21 | 5.0 |
| H93Y/F94Y | 69.4 ± 0.11 | 7.6 |
| H93Y/L356H | 70.4 ± 0.02 | 8.7 |
| H93Y/A389P | 71.9 ± 0.09 | 10.1 |

TABLE 2-continued $T_m$ values of the wild and the mutant mannanase

| variant | $T_m$ (° C.) | $\Delta T_m$ (° C.) |
|---|---|---|
| L356H/A389P | 67.4 ± 0.10 | 5.6 |
| H93Y/F94Y/L356H | 69.7 ± 0.28 | 7.9 |
| H93Y/L356H/A389P | 75.3 ± 0.08 | 13.5 |
| H93Y/F94/L356H/A389P | 75.5 ± 0.12 | 13.8 |

As shown in Table 2, the $T_m$ values of the wild mannanase Pman5A was 61.8° C., and those of the single site mutation mutants H93Y and A389P were 69.2° C. and 66.8° C., which were increased by 7.5° C. and 5.0° C. comparing that of the wild mannanase respectively. And, the $T_m$ value of said two sites combination mutation mutant was increased to 71.9° C. which was 10.1° C. higher than that of the wild mannanase Pman5A, demonstrating the importance of the sites of H93 and A389 for the thermal stability of the wild mannanase Pman5A and the stack effect.

Although the $T_m$ values of the mutants F94Y and L356H were increased comparing that of the wild mannanase Pman5A, when combined with the other sites, the obtained mutants showed the stack effect of the $T_m$ values. For example, the $T_m$ value of the mutant H93Y/L356H/A389P was 75.3° C., and increased by 0.3° C. when combined with the mutation of F94Y.

(3) Determination of T50 Value and Half-Life of Mutant and Wild Mannanase

The mutant and wild mannanase were diluted to 70 μg/mL with Na$_2$HPO$_4$-citric acid buffer at pH 5.0, followed by being treated for 30 min at the different temperatures of 60 to 80° C. without the substrate, and being putting on the ice to determine the remaining activity at pH 5.0 and their optimum temperatures. The results were shown in Table 3.

The mutant and wild mannanase were diluted to 70 μg/mL with Na$_2$HPO$_4$-citric acid buffer at pH 5.0, followed by being treated for 30 min at the temperatures of 70° C., 75° C. and 80° C. without the substrate, and being putting on the ice to determine the remaining activity at pH 5.0 and their optimum temperatures and calculate the time of the remaining enzyme activity being half of the highest enzyme activity at a certain temperature, which was half-life at such temperature. The results were shown in Table 3.

TABLE 3

$T_{50}$ and $t_{1/2}$ values of the wild and the mutant enzyme

| | $T_{50}$ (° C.) | $t_{1/2}$ (min) | | |
|---|---|---|---|---|
| | | 70° C. | 75° C. | 80° C. |
| Pman5A | 66 | 4 | 2 | — |
| H93Y | 73 | 64 | 10 | 3 |
| F94Y | 66 | 4 | 2 | — |
| L356H | 68 | 14 | 4 | — |
| A389P | 70 | 45 | 5 | 2 |
| H93Y/F94Y | 73 | 75 | 17 | 3 |
| H93Y/L356H | 75 | / | 55 | 5 |
| H93Y/A389P | 79 | / | 120 | 14 |
| L356H/A389P | 70 | 31 | 5 | 3 |
| H93Y/F94Y/L356H | 76 | / | 47 | 5 |
| H93Y/L356H/A389P | 79 | / | 120 | 14 |
| H93Y/F94/L356H/A389P | 80 | / | 180 | 27 | wherein "/" indicates that the treatment time is too long to be determined; and "—" indicates there is no enzyme activity within 2 min of treatment As shown in Table 3, the $T_{50}$ values of the wild mannanase Pman5A was 66° C., and those of the single site mutation mutants H93Y, L356H and A389P were 73° C., 68° C. and 70° C. which were increased by 7.0° C., 2.0° C. and 4° C. comparing that of the wild mannanase Pman5A, respectively, while the $T_{50}$ value of the mutant F94Y kept unchanged, thus demonstrating that the mutations of H93Y, L356H and A389P were the keys for improving the thermal stability of the wild mannanase of GH5 family and generated a stack effect.

And, the $T_{50}$ values of the combination mutation mutants H93Y/L356H and H93Y/A389P were increased by 2° C. and 6° C. compared that of the mutant H93Y, and the $T_{50}$ value of the combination mutation mutant L356H/A389P was increased by 2° C. compared with that of the mutant L356H, thus demonstrating that the combination mutation mutants showed the stack effect to the thermal stability.

The multi-sites combination mutation mutant H93Y/F94Y/L356H, H93Y/L356H/A389P and H93Y/F94Y/56H/A389P showed the improved thermal stability, and had the $T_{50}$ values of 76° C., 79° C. and 80° C. which were 10° C., 13° C. and 14° C. higher than that of the wild mannanase Pman5A.

And, $t_{1/2}$ values of the four single-site mutation mutants H93Y, F94Y, L356H and A389P were 64 min, 4 min, 14 min and 45 min at 70° C., showing the improvement of the thermal stability, and the thermal stability of the combination mutation mutants ranked as the mutant L353/A389P<the mutant H93Y/F94Y<the mutant H93Y/F94Y/L356H<the mutant H93Y/A389P<the mutant H93Y/L356H/A389P<the mutant H93Y/F94Y/L356H/A389P at 75° C., demonstrating the stack effect of the combination mutation mutants to the improvement of the thermal stability, wherein the mutant H93Y/F94Y/L356H/A389P had the best thermal stability of remaining half of the enzyme activity after being treated for 3 h at 75° C., and had a half-life of 27 min at 80° C.

(4) Determination of the Kinetic Parameters of the Mutant and Wild Mannanase

The enzyme activity was determined by reacting for 5 min at 85° C., 80° C. and 70° C. and pH5.0 using the different concentrations of locust bean gum in 5 mg/mL, 2.5 mg/mL, 2 mg/mL, 1 mg/mL, 0.75 mg/mL, 0.5 mg/mL, and 0.375 mg/mL as the substrate, and the $K_m$ value and $V_{max}$ value were calculated with software GraFit7. The results were shown in Table 4.

TABLE 4 the kinetic parameters of the mutant and wild mannanase

| | $K_m$ (mg mL$^{-1}$) | $V_{max}$ (μmol min$^{-1}$ mg$^{-1}$) | kcat/$K_m$ (mL s$^{-1}$ mg$^{-1}$) | Specific activity (U mg$^{-1}$) |
|---|---|---|---|---|
| Pman5A | 0.51 | 1115 | 1628 | 1276 |
| H93Y | 0.68 | 1862 | 2066 | 1537 |
| F94Y | 0.87 | 2048 | 1758 | 1612 |
| L356H | 0.87 | 2489 | 2155 | 1237 |
| A389P | 0.86 | 1679 | 1471 | 1609 |
| H93Y/F94Y | 0.70 | 1941 | 2067 | 1769 |
| H93Y/L356H | 0.68 | 2046 | 2263 | 1585 |
| H93Y/A389P | 0.81 | 2261 | 2081 | 1742 |
| L356H/A389P | 0.73 | 1977 | 2039 | 1712 |
| H93Y/F94Y/L356H | 0.73 | 2468 | 2549 | 1921 |
| H93Y/L356H/A389P | 0.58 | 1641 | 2134 | 2202 |
| H93Y/F94/L356H/A389P | 0.67 | 2225 | 2485 | 2226 |

As shown in Table 4, the catalytic efficiency of all the mutants were improved compared with that of the wild mannanase Pman5A, wherein the improvement of the catalytic efficiency of the mutants ranked as the single site mutation mutant<double-sites mutation mutant<multiple-sites mutation mutant. The specific activity was increased from 1276 U/mg of the wild mannanase Pman5A to 2226 U/mg of the combination mutation mutants H93Y/F94Y/L356H/A389, which increased by about 0.7 times, and the catalytic efficiency was increased by 0.5 times.

The invention claimed is:

1. A mannanase mutant comprising a substitution at amino acid residue 93 of said mannanase mutant, wherein the mannanase mutant is a PMan5A having the amino acid sequence of SEQ ID NO: 2, wherein histidine is substituted with tyrosine at amino acid residue 93, and wherein said mannanase mutant has improved thermal stability and further comprises a substitution at amino acid residues 94, and/or 356, and/or 389.

2. The mannanase mutant of claim 1, wherein phenylalanine is substituted with tyrosine at amino acid residue 94, and/or leucine is substituted with histidine at amino acid residue 356, and/or alanine is substituted with proline at amino acid residue 389.

3. The mannanase mutant of claim 1, wherein said mannanase mutant is recombinantly prepared by: (1) transforming a host cell with a recombinant vector comprising a gene encoding the mannanase mutant to obtain a recombinant strain;
(2) culturing the recombinant strain and inducing to express a recombinant mannanase mutant; and
(3) recovering and purifying the recombinant mannanase mutant.

* * * * *